United States Patent [19]

Penny et al.

[11] 3,965,901
[45] June 29, 1976

[54] SUCTION CATHETER
[75] Inventors: William Henry Penny, Arcadia; Edmund E. Spaeth, Glendale, both of Calif.
[73] Assignee: American Hospital Supply Corporation, Evanston, Ill.
[22] Filed: Oct. 3, 1974
[21] Appl. No.: 511,622

[52] U.S. Cl. ............................ 128/276; 128/350 R
[51] Int. Cl.² .................................... A61M 1/00
[58] Field of Search ........... 128/276, 350, 351, 349, 128/239, 277, 278, 240, 348; 32/33

[56] References Cited
UNITED STATES PATENTS

| | | | |
|---|---|---|---|
| 2,574,135 | 11/1951 | Ward | 32/33 |
| 3,090,122 | 5/1963 | Erickson | 32/33 |
| 3,460,255 | 8/1969 | Hutson | 32/33 |
| 3,506,010 | 4/1970 | Murr | 128/276 |
| 3,517,669 | 6/1970 | Buono et al. | 128/276 |
| 3,528,427 | 9/1970 | Sheridan et al. | 128/276 X |
| 3,661,144 | 5/1972 | Jensen et al. | 128/276 X |
| 3,810,471 | 5/1974 | Truhan | 128/276 |
| 3,848,604 | 11/1974 | Sackner | 128/350 R |

*Primary Examiner*—John D. Yasko
*Attorney, Agent, or Firm*—Larry N. Barger; Robert T. Merrick

[57] ABSTRACT

An improved flexible catheter for suctioning of tracheobronchial passages. In one form, the catheter is provided with side openings which are elongated in a direction generally parallel to the end surface of the tubular member, and are located adjacent thereto. The catheter may be provided with a beveled tip, in which case a second form of the invention is advantageously provided with side openings which are elongated longitudinally of the catheter, and located adjacent the top portion thereof. In a third form of the invention, the catheter has triangular side openings which combine the advantages of both of the foregoing forms of the invention. Effectiveness of the catheter is further improved by restricting the area of the end openings so that the total area of the side openings is from 1.5 to 6 times the area of the end opening. Longitudinal slots along the outer surface of the catheter, adjacent to the side holes relieve the suction and reduce tissue trauma when openings are blocked.

12 Claims, 16 Drawing Figures

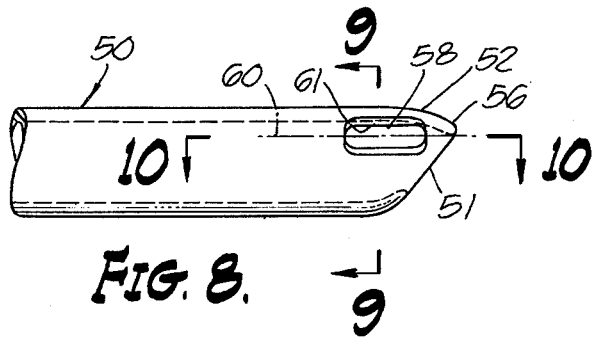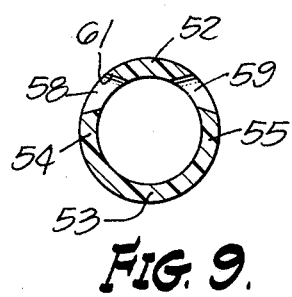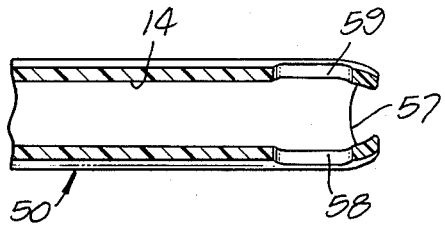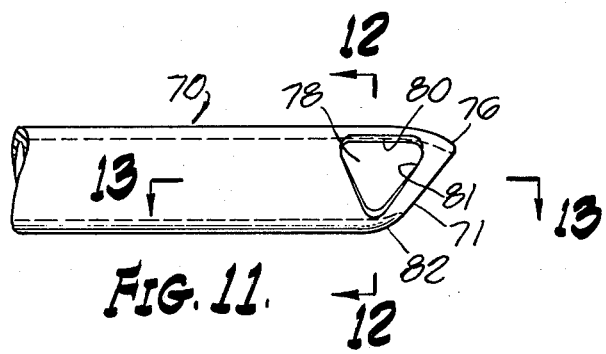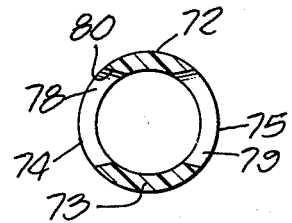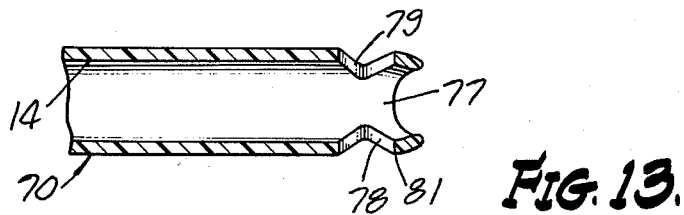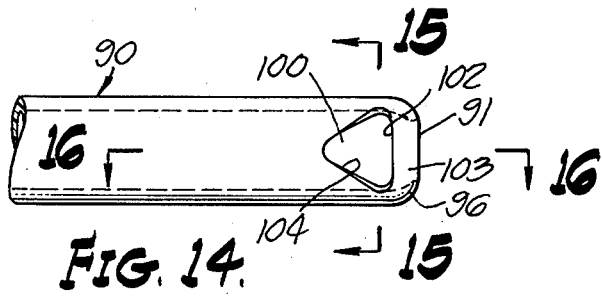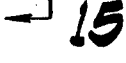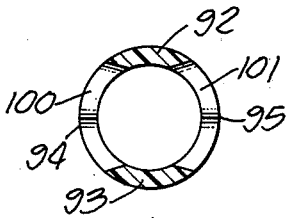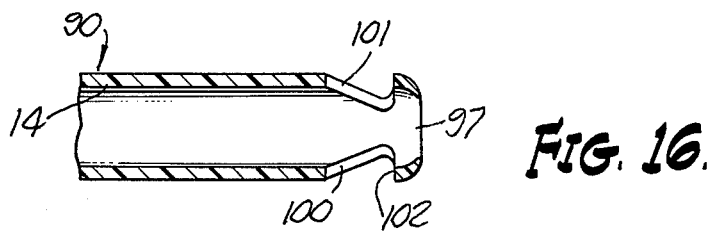

SUCTION CATHETER

BACKGROUND OF THE INVENTION

This invention relates to suction catheters for aspiration of mucus and other fluids from the tracheobronchial passages, and particularly to catheters having improved tip structures which allow more efficient suctioning of the entrances to the bronchial tubes, and which reduce the likelihood of trauma during the suctioning procedure.

Traditionally, suction catheters have consisted of a flexible plastic tube having a beveled end, an end opening, and an opening spaced substantially back from the beveled end and passing through the top wall section, that is, the wall section which extends to form the tip of the beveled end. Such catheters have been relatively inefficient in some orientations in that air passing through the second opening reduces the suction available at the end opening. Moreover, the high degree of suction at the top opening when the end opening is occluded is apt to cause trauma to delicate tissues. See for example, the article entitled, "Pathogenesis and Prevention of Tracheobronchial Damage With Suction Procedures" appearing in the September, 1973 issue of CHEST (64 Chest 284 – 290).

Various catheter designs have been proposed, but these generally have a flat, rather than a beveled end. The lack of a beveled end makes such catheters more difficult to guide, particularly past the epiglottis into the trachea, and subsequently into the left mainstem bronchus, which is more difficult to reach than the right because of its sharper angle of bifurcation.

References indicating the state of the prior art include U.S. Pat. Nos. 3,319,628, 3,375,828, 3,407,817, 3,517,669, 3,590,820 and design U.S. Pat. No. 223,247.

It is therefore, an object of the invention to provide a more efficient and less traumatic catheter, which can be more easily directed into the desired bronchial passages.

Another object of the invention is to provide a suction catheter which will effectively aspirate thick bronchial mucus, without unduly traumatizing delicate tissues. Other objects and advantages of the invention will become apparent from the following discussion.

SUMMARY OF THE INVENTION

These and other objects are met by a suction catheter having an end opening and at least one side opening. The side opening is elongated in a direction generally parallel to the end surface of the catheter, and is located immediately adjacent thereto, so as to provide a maximum of side opening area as close as possible to the end opening.

The suction catheter may be provided with a beveled end surface which can be more easily directed into the desired tracheobronchial passages. In this case, the catheter is advantageously provided with a side opening which is elongated longitudinally of the catheter and located adjacent the top portion thereof.

In a third form of the invention, the catheter has a triangular side opening which combines the advantages of both of the foregoing forms of the invention, and thus provides the optimum of suctioning efficiency while at the same time minimizing potential trauma to sensitive tissues.

Effectiveness of the catheter is further improved by restricting the end opening so that its area is less than the cross-sectional area of the longitudinal passage through the catheter, and is less than the total area of the side openings. In the preferred design, the total area of the side openings is from 1.5 to 6 times the area of the end opening.

Longitudinal slots may be provided along the outer surface of the catheter adjacent to the side holes to relieve the suction and reduce tissue trauma when openings are blocked.

BRIEF DESCRIPTION OF THE DRAWINGS

FIG. 8 is an enlarged elevational view of the distal end of the catheter, showing another modified form of the invention;

FIG. 9 is a vertical sectional view on the line 9 — 9 of FIG. 8;

FIG. 10 is a horizontal sectional view on the line 10 — 10 of FIG. 8;

FIG. 11 is an enlarged elevational view of the distal end of a further modified form of the invention;

FIG. 12 is a vertical sectional view on the line 12 — 12 of FIG. 11;

FIG. 13 is a horizontal sectional view on the line 13 — 13 of FIG. 11;

FIG. 14 is an enlarged elevational view of the distal end of a still further form of the invention;

FIG. 15 is a vertical sectional view on the line 15 — 15 of FIG. 14;

FIG. 16 is a horizontal sectional view on the line 16 — 16 of FIG. 14;

DESCRIPTION OF PREFERRED EMBODIMENTS

Figure 1:
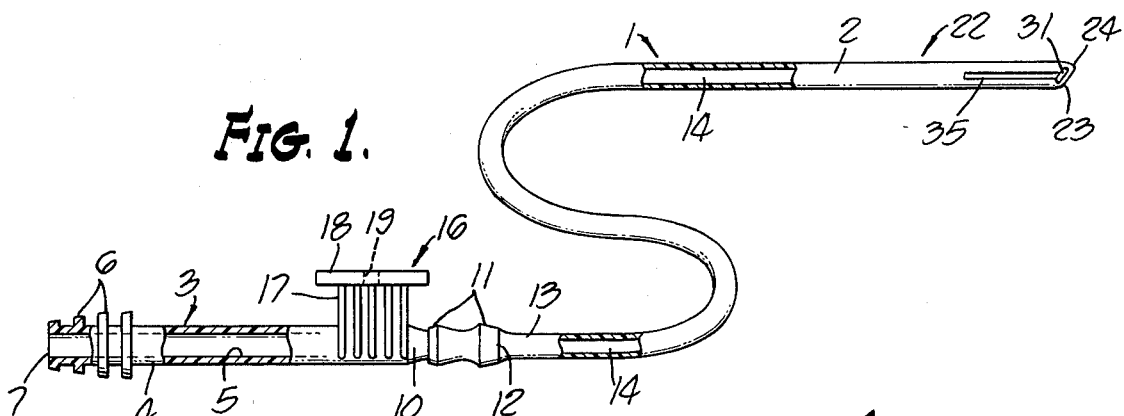
FIG. 1 is an elevational view, partially broken-away, of one form of the suction catheter of this invention.

Referring now to FIGS. 1 through 5, suction catheter 1 has a flexible tubular body 2 and a rigid connector 3 having a tubular body 4. Axial passage 5 extends longitudinally through body 4, terminating at the end of the body in a suction port 7. Annular ribs 6 on the outer surface of body 4 facilatate firm attachment of a tube (not shown), the other end of which is attached to a suction source.

The end of connector 3 opposite suction port 7 has a tubular extension 10 with external retaining rigs 11 over which the proximal end section 13 of flexible tubular member 2 is telescoped. At this end, connector 3 passage 5 terminates in a catheter port 12 which communicates with the longitudinal passage or lumen 14 of flexible tubular member 2.

Connector 3 is provided with a regulator 16 having an upstanding cylindrical body 17, and a planar top 18. An opening or atmospheric port 19 in the planar top 18 is connected by a passage (not shown) through body 17 to axial passage 5. In this way, the operator can control the degree of suction available at catheter port 12 by opening and closing the atmospheric port 19 with his finger.

The distal end section 22 of flexible tubular member 2 terminates in a beveled end surface 23 which lies in a plane oblique to the axis of tubular member 2. Therefore, the top wall section of tubular member 2 terminates in a tip 24 which extends beyond or overhangs the end of the bottom wall section. An annular inwardly curving wall section 25 provides the end of the catheter with a smooth rounded end surface, and defines an axial end opening 26, having an area smaller than the cross-sectional area of lumen 14.

At least one, and preferably two, side openings 31, 32 are provided in the opposed side walls of tubular member 2, and communicate with lumen 14. Side openings 31 and 32 are preferably oval or rectangular in shape and the major axis or center line 33 is generally parallel to the plane of beveled end surface 23. Moreover, side openings 31, 32 should be located as close as possible to beveled end surface 23, so as to minimize the width of the wall section 34 which lies between the front edge 37 of opening 31 and the beveled end surface 23. For example, wall section 34 is preferably from 0.020 inch to 0.10 inch (0.5 to 2.5 millimeters) wide.

If desired, distal end section 22 may also be provided with a rear suction relief channel 35 extending one-half inch or more along the exterior surface of distal end section 22 from side opening 31 towards the proximal end of tubular member 2. Likewise, relief channel 36 may be provided rearwardly of, and communicating with side opening 32. To assure an open channel, the channels 35, 36 should be relatively narrow. For example, a channel having a depth of 0.010 to 0.015 inch (0.25 to 0.38 mm) preferably has a width of from 0.02 to 0.050 inch (0.5 to 1.27 millimeters). Relief channels 35 and 36 serve to reduce the suction, and, therefore, the trauma which may be caused, when the catheter enters a small bronchial passage where the complete tip, or a major portion thereof may be occluded.

It should be noted that side openings 31, 32 are located as close as possible to beveled end surface 23, so that a relatively large side opening can be used without relieving so much of the suction that end opening 26 is ineffective. Moreover, restriction of end opening 26 by the annular inwardly curving wall section 25 assures that adequate suction is available through side openings 31, 32. Since the major portions of the side openings, as well as the entire end opening, are all located near the very tip of the catheter, liquid entering any of the three openings as the catheter enters a pool of liquid, bridges across lumen 14. This results in the liquid being sucked rapidly up the catheter.

Figure 6:
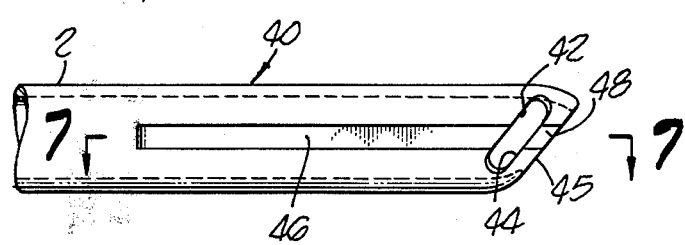
FIG. 6 is an enlarged elevational view of the distal end of the catheter, showing a modified form of the invention.
Figure 7:
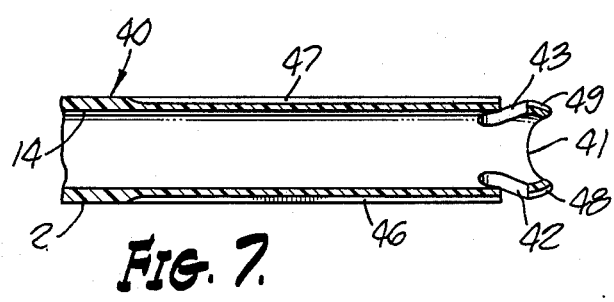
FIG. 7 is a horizontal sectional view on the line 7 — 7 of FIG. 6.

FIGS. 6 and 7 show the distal end section 40 of a modified form of the invention. In this form, end section 40 has an end opening 41 and side openings 42 and 43. Rear suction relief channels 46 and 47 extend from side openings 42 and 43 respectively toward the proximal end of tubular member 2.

In this embodiment forward relief channels 48 and 49 provide an exterior passageway from openings 42 and 43 respectively forward to the beveled end surface 45. These relief channels allow mucus and other fluid to be aspirated from in front of the catheter, even though end opening 41 may be occluded by tissues.

The forms of the invention thus far described are particularly effective for suctioning of the trachea and mainstem bronchi. For deeper suctioning as for example suctioning of entrances to the bronchial tubes, the embodiment of the invention shown in FIGS. 8 through 10 has certain advantages in that additional protection is provided against occlusion of both the end and side openings in the narrow passages present in this area, and therefore against resulting trauma to these tissues. As shown in FIGS. 8 through 10, distal end section 50 of the catheter again has a beveled end surface 51 so that the top wall section 52 of tubular member 2 projects beyond side wall sections 54 and 55 and bottom wall section 53 to form an extending tip 56. End section 50 also has an end opening 51 and side openings 58 and 59.

In this form of the invention, side opening 58 is preferably elongated longitudinally along member 2 so that the major axis or center line is substantially parallel to the axis of member 2. Opening 58 may be either oval or rectangular in shape. The upper edge 61 of side opening 58 is preferably located as close as possible to the top wall section 52 so that the longitudinal center line 60 of the opening is generally parallel to, but spaced upwardly from, the axis of tubular member 2.

It should be noted that in this form of the invention a major portion of the area of the side opening 58 is offset toward the top wall section 52 from a plane passing through the respective centers of the side wall sections 54, 55. Thus side opening 58 is particularly effective in suctioning mucus when the catheter is in an inverted position. In the position shown in FIG. 8, effective suctioning is provided through end opening 57. In both positions, the portion of side opening 58 spaced furthest from end surface 51 relieves the suction and minimizes tissue trauma should end opening 57 be occluded.

As shown in FIGS. 11 through 13, the advantages of the forms of the invention thus far illustrated can be combined in a single catheter by use of a triangular-shaped side opening. Thus, the distal end section 70 has a beveled end surface 71 defining an end opening 77. Top wall section 72 extends beyond bottom wall section 73 and side wall sections 74 and 75, to provide an extending tip 76.

Figure 2:
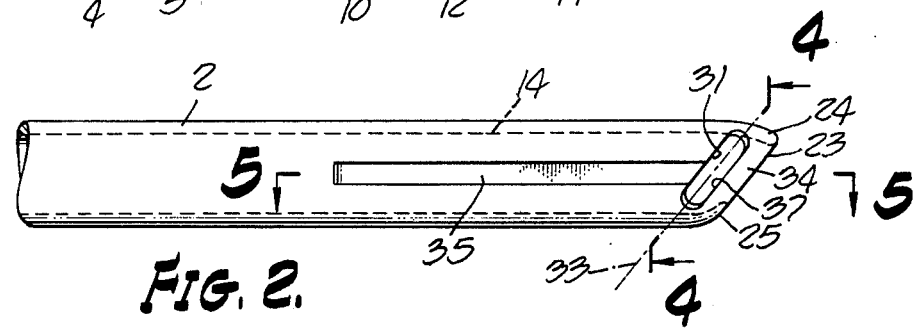
FIG. 2 is an enlarged elevational view of the distal end of the catheter shown in FIG. 1.
Figure 3:
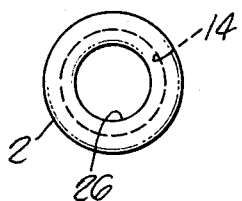
FIG. 3 is an end elevational view as seen from the right side of FIG. 2.
Figure 4:
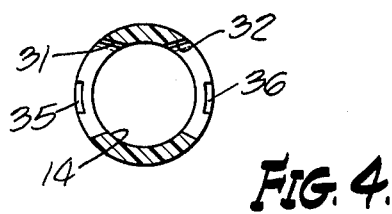
FIG. 4 is a vertical sectional view on the line 4 — 4 of FIG. 2.
Figure 5:
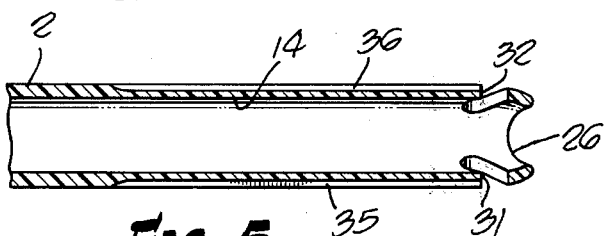
FIG. 5 is a horizontal sectional view on the line 5 — 5 of FIG. 2.

Side openings 78 and 79 are triangular in shape. The front edge 81 of opening 78 is generally parallel to beveled end surface 71 and is located as close thereto as practical. It should be noted that the length of front edge 81 is substantially equal to the length of the front edge 37 of opening 31, as shown in FIG. 2. Also, the upper edge 80 is located as close as practical to top wall section 72, and the length of edge 80 is substantially equal to the length of upper edge 61 of opening 58 as shown in FIG. 8. Thus, this embodiment incorporates the advantages of both of these previously described embodiments, and a catheter is obtained which has outstanding advantages for suctioning of the trachea, the mainstem bronchi, and the subsidiary bronchi.

The form of the invention shown in FIGS. 11 through 13 also has an annular inwardly curving wall section 82 which provides the catheter with a smooth rounded end surface, and which restricts the axial end opening 57 so that its area is substantially less than the cross-sectional area of lumen 14. This restriction of the area of the end opening results in a surprising increase in the efficiency of the suctioning process.

For example, six catheters having end openings of diameter of 0.015 inch to 0.128 inch (0.38 to 3.24 millimeters) and each having two triangular shaped side holes with a total area of 0.008 square inch (5.2 square millimeters) were compared in a laboratory test in which suction was applied to the catheter, and the catheter was drawn lengthwise through a trough of a viscous simulated mucus.

TABLE I

| END OPENING | | SIDE OPENINGS | RATIO OF SIDE TO END | UPTAKE RATE |
|---|---|---|---|---|
| DIAMETER | AREA | AREA | OPENING AREA | Grams/ |
| (Inch) | (Square Inch) | (Square Inch) | | Second |
| .015 (0.38mm) | .00018 (12 sq.mm) | .008 (5.2 sq.mm) | 45 | .63 |
| .031 (0.79mm) | .00075 (.48 sq.mm) | .008 (5.2 sq.mm) | 10.6 | .59 |
| .047 (1.2mm) | .0017 (1.1 sq.mm) | .008 (5.2 sq.mm) | 4.6 | .57 |
| .082 (2.1mm) | .0053 (3.4 sq.mm) | .008 (5.2 sq.mm) | 1.5 | .38 |
| .102 (2.6mm) | .0082 (5.3 sq.mm) | .008 (5.2 sq.mm) | 0.93 | .28 |
| .128 (3.3mm) | .0129 (8.3 sq.mm) | .008 (5.2 sq.mm) | 0.63 | .22 |

As shown in Table 1, the liquid uptake rate increases rapidly as the end hole diameter is decreased from 0.128 to 0.047 inch (3.3 to 1.2 millimeters). In terms of the ratio of the total area of the side holes to the area of the end holes (see column 4 of Table 1) efficient liquid uptake is obtained at a ratio of approximately 1.5. Liquid uptake reaches a maximum at a ratio of approximately 5 and increases only slowly at higher ratios. Since the higher ratios require very large side holes which may weaken the catheter, or unduly restricted end holes which would reduce suctioning effectiveness in small bronchial passages where side openings may be largely occluded, the ratio of side opening area to end opening area should preferably be 6 or less.

In some cases, it may be desirable to use a blunt end catheter rather than the beveled end catheter which is usually preferred. Suprisingly, the triangular side opening also has advantages in the blunt end type of catheter. As shown in FIGS. 14 through 16, distal end section 90 has a transverse end surface which lies in a plane substantially at 90° to axis of tubular member 2. As a result, top wall section 92 does not project beyond the bottom wall section 93 and side wall sections 94 and 95, as in the previously described embodiments. A smooth rounded tip is, however, provided by the annular inwardly curving wall section 96, which also defines an end opening 97 having a lesser diameter than the lumen of tubular member 2.

Triangular side openings 100 and 101 are located as far forward as practical, so that the width of wall section 103 between the front edge 102 of opening 100 and transverse end surface 91 is reduced to a minimum.

Thus, a side opening is provided which has a maximum of suctioning area as close as possible to the end of the catheter. This construction provides effective suctioning near the tip of the catheter, even if the end opening is blocked by tissue. This is particularly important in the suctioning of thick, viscous mucus which sometimes occurs in the tracheobronchial passages. Since the mucus will be drawn into the forward portion of the side opening which portion includes the majority of the flow area, a high "rate of closure" of the side opening will thus be provided, and undue amounts of air will not be sucked in so as to unduly reduce the available suction force.

While in the foregoing, several forms of the invention have been disclosed in considerable detail for purposes of illustration, it will be understood by those skilled in the art that many of these details may be varied without departing from the spirit and scope of the invention.

We claim:

1. A medical suction catheter with a generally cylindrical flexible tube having a longitudinal bore extending between a front opening and a rear opening connected to a suction regulator, wherein the improvement comprises:
said flexible tube having two side openings with at least some portions of these side openings diametrically opposed from each other near the front opening, and each side opening has an area greater than one half the front opening's area, with the flexible tube between its front and rear openings being devoid of any other opening of equal or greater area than either one of its side openings, so that the front and side openings can coordinate suction forces for rapid removal of mucus from delicate tracheobronchial tissue to minimize suction damage to such tissue.

2. A medical suction catheter as set forth in claim 1, wherein the flexible tube has a beveled front end surface, and there is an overhanging forward tip along a top wall of the tube.

3. A medical suction catheter as set forth in claim 1, wherein the tube has external channels leading to the side openings.

4. A medical suction catheter as set forth in claim 1, wherein the tube has an internal constriction at a front opening making the front opening smaller than the tube's bore.

5. A catheter as set forth in claim 1 wherein said side openings are oval shaped.

6. A catheter for suctioning of tracheobronchial passages comprising:
a. a tubular body having a longitudinal axis and two ends, one end being attached to a connector, and the other end terminating in an end surface defining a plane;
b. the tubular body having an end opening in said end surface communicating with a longitudinal passage extending through said tubular body, and the open area of the end opening is less than the cross-sectional area of the passage; and
c. at least one opening through the side of the tubular body, said opening being elongated in a direction generally parallel to the plane of said end surface, and the total area of the side openings is from 1.5 times to 6 times that of the end opening.

7. A catheter for suctioning of tracheobronchial passages comprising:
a. a tubular body having two ends and a longitudinal passage therethrough, one end being attached to a connector, and the other end terminating in an end surface defining a plane;
b. at least one opening through a side of the tubular body communicating with the longitudinal passage therethrough, said opening being triangular in shape and having one side generally parallel to the end surface; and c. the tubular body has an end opening in said end surface communicating with the longitudinal passage extending through said tubular body and the open area of the end opening is less than the cross-sectional area of the passage, and the total area of the side openings is from 1.5 times to 6 times that of the end opening.

8. A catheter as set forth in claim 7 wherein a second side of the triangular side opening is generally parallel and adjacent to the top section of the tubular body wall.

9. A catheter for suctioning of tracheobronchial passages comprising:
 a. a flexible tubular member having a distal end, a proximal end, and a longitudinal passage;
 b. a rigid connector attached to the proximal end of said tubular member, and having an axial passage extending from a suction port to and communicating with the longitudinal passage of the tubular member;
 c. means adjacent said suction port for attaching a vacuum source;
 d. regulator means on said connector, said means having a passage communicating with the axial connector passage at one end, and with an atmospheric port at the opposite end;
 e. beveled end surface on the distal end of the tubular member, said surface lying in a plane oblique to the axis of the tubular member;
 f. an extending tip formed by the portion of the top wall of the tubular member lying in the plane of the beveled end surface;
 g. an opening through said beveled end surface, and having an open area less than the cross-sectional area of the longitudinal passage;
 h. a pair of opposed triangular openings through the side walls of the tubular member and communicating with the longitudinal passage, the sides of said opening being substantially of the same orientation, and one of said sides of each triangular opening being substantially parallel to the plane of the beveled end surface.

10. A catheter for suctioning of tracheobronchial passages comprising:
 a. a flexible tubular member having a distal end, a proximal end, and a longitudinal passage;
 b. a rigid connector attached to the proximal end of said tubular member, and having an axial passage extending from a suction port to and communicating with the longitudinal passage of the tubular member;
 c. means adjacent said suction port for attaching a vacuum source;
 d. regulator means on said connector, said means having a passage communicating with the axial connector passage at one end, and with an atmospheric port at the opposite end;
 e. beveled end surface on the distal end of the tubular member, said surface lying in a plane oblique to the axis of the tubular member;
 f. an extending tip formed by the portion of the top wall of the tubular member lying in the plane of the beveled end surface;
 g. an opening through said beveled end surface, and having an open area less than the cross-sectional area of the longitudinal passage;
 h. at least one opening through the side wall of the tubular member and communicating with the longitudinal passage, the sides of said opening being substantially equal in length, and one of said sides being substantially parallel to the plane of the beveled end surface; and the total area of the side openings is at least 1.5 times the area of the end opening.

11. A catheter for suctioning of tracheobronchial passages comprising:
 a. a flexible tubular member having a distal end, a proximal end, and a longitudinal passage;
 b. a rigid connector attached to the proximal end of said tubular member, and having an axial passage extending from a suction port to and communicating with the longitudinal passage of the tubular member;
 c. means adjacent said suction port for attaching a vacuum source;
 d. regulator means on said connector, said means having a passage communicating with the axial connector passage at one end, and with an atmospheric port at the opposite end;
 e. beveled end surface on the distal end of the tubular member, said surface lying in a plane oblique to the axis of the tubular member;
 f. an extending tip formed by the portion of the top wall of the tubular member lying in the plane of the beveled end surface;
 g. an opening through said beveled end surface, and having an open area less than the cross-sectional area of the longitudinal passage;
 h. at least one opening through the side wall of the tubular member and communicating with the longitudinal passage, the sides of said opening being substantially equal in length, and one of said sides being substantially parallel to the plane of the beveled end surface, and a second side of said opening runs longitudinally along the tubular member and is generally parallel and adjacent to the top wall section of said member so that a major portion of the area of said side opening is offset toward said top wall section from a plane passing through the respective centers of the wall sections.

12. A suction catheter for suctioning tracheobronchial passages comprising:
 a. a flexible tubular body having a longitudinal passage therethrough;
 b. a mucus inlet end opening communicating with said passage, and having an area less than the cross-sectional area of the passage; and
 c. two opposed mucus inlet openings through the side walls of the tubular body, the total area of these two side wall openings being from 1.5 to 6 times the area of the end opening, and said tube being devoid of any other mucus inlet opening of equal or greater area than either side opening, whereby the three mucus inlet openings can coordinate suction forces for rapid removal of mucus from delicate tracheobronchial tissue to minimize suction damage to such tissue.

* * * * *